(12) United States Patent
Sakata et al.

(10) Patent No.: US 7,640,047 B2
(45) Date of Patent: Dec. 29, 2009

(54) TEST INSTRUMENT, ATTACHMENT, AND CONCENTRATION MEASURING APPARATUS

(75) Inventors: Tetsuya Sakata, Kyoto (JP); Daisuke Matsumoto, Kyoto (JP); Yasuhide Kusaka, Kyoto (JP)

(73) Assignee: Arkray, Inc., Kyoto (JP)

( * ) Notice: Subject to any disclaimer, the term of this patent is extended or adjusted under 35 U.S.C. 154(b) by 482 days.

(21) Appl. No.: 10/489,397

(22) PCT Filed: Sep. 6, 2002

(86) PCT No.: PCT/JP02/09132

§ 371 (c)(1),
(2), (4) Date: Mar. 10, 2004

(87) PCT Pub. No.: WO03/025559

PCT Pub. Date: Mar. 27, 2003

(65) Prior Publication Data

US 2004/0242982 A1 Dec. 2, 2004

(30) Foreign Application Priority Data

Sep. 11, 2001 (JP) ............................. 2001-275532

(51) Int. Cl.
*A61B 5/05* (2006.01)

(52) U.S. Cl. ..................... 600/345; 600/573; 204/403.1

(58) Field of Classification Search ................. 600/345; 422/100, 102; 436/180; 204/403
See application file for complete search history.

(56) References Cited

U.S. PATENT DOCUMENTS 5,065,768 A * 11/1991 Coleman et al. ............ 600/573
5,147,606 A * 9/1992 Charlton et al. ............. 422/56
5,437,999 A * 8/1995 Diebold et al. ......... 204/403.11

(Continued)

FOREIGN PATENT DOCUMENTS

JP         63-180837         7/1988

(Continued)

*Primary Examiner*—Patricia C Mallari
*Assistant Examiner*—Karen E Toth
(74) *Attorney, Agent, or Firm*—Hamre, Schumann, Mueller & Larson, P.C.

(57) ABSTRACT

The present invention relates to a test instrument (X) including a capillary (5) for moving a sample liquid (B), a liquid pooling portion (4) communicating with the capillary (5) for retaining the sample liquid (B) to be introduced into the capillary (5), and a liquid introduction selector (12) for selecting whether or not the sample liquid (B) retained in the liquid pooling portion (4) is introduced into the capillary (5). The present invention also relates to an attachment provided with the test instrument (X), and a concentration measuring apparatus to which the attachment is mounted for use.

7 Claims, 14 Drawing Sheets

U.S. PATENT DOCUMENTS

| | | | |
|---|---|---|---|
| 5,800,420 A * | 9/1998 | Gross et al. | 604/890.1 |
| 5,843,691 A * | 12/1998 | Douglas et al. | 435/14 |
| 6,001,307 A * | 12/1999 | Naka et al. | 422/81 |
| 6,048,352 A * | 4/2000 | Douglas et al. | 606/181 |
| 6,315,738 B1 * | 11/2001 | Nishikawa et al. | 600/583 |
| 6,368,563 B1 | 4/2002 | Allen et al. | |
| 6,406,919 B1 | 6/2002 | Tyrrell | |
| 6,575,188 B2 * | 6/2003 | Parunak | 137/251.1 |
| 6,878,262 B2 * | 4/2005 | Taniike et al. | 205/777.5 |
| 7,025,774 B2 * | 4/2006 | Freeman et al. | 606/181 |
| 7,238,534 B1 * | 7/2007 | Zimmer | 436/169 |
| 7,294,310 B2 * | 11/2007 | Yamazaki et al. | 422/100 |
| 2002/0198444 A1 * | 12/2002 | Uchigaki et al. | 600/345 |
| 2003/0083685 A1 * | 5/2003 | Freeman et al. | 606/181 |
| 2003/0109808 A1 * | 6/2003 | Takinami et al. | 600/584 |
| 2004/0072357 A1 * | 4/2004 | Stiene et al. | 436/69 |
| 2006/0131171 A1 * | 6/2006 | Kobayashi | 204/403.01 |
| 2006/0188410 A1 * | 8/2006 | Ishida et al. | 422/102 |

FOREIGN PATENT DOCUMENTS

| | | |
|---|---|---|
| JP | 8-304336 | 12/1996 |
| JP | 9-266898 | 10/1997 |
| JP | 10-24028 | 1/1998 |
| JP | 11-347018 | 12/1999 |
| JP | 2000-231 | 1/2000 |
| JP | 2000-258382 | 9/2000 |
| WO | 00/54047 | 9/2000 |
| WO | 01/43796 | 6/2001 |

* cited by examiner

TEST INSTRUMENT, ATTACHMENT, AND CONCENTRATION MEASURING APPARATUS

TECHNICAL FIELD

The present invention relates to a test instrument used for measuring the concentration of a particular component contained in a sample liquid, while also relating to an attachment provided with such a test instrument and further to a concentration measuring apparatus to which such an attachment is mounted for use.

BACKGROUND ART

A blood glucose level measuring apparatus, an example of concentration measuring apparatus, employs a popular method for measuring the concentration of glucose contained in blood, the method utilizing oxidation-reduction reaction using oxidoreductase as the catalyst. In using the blood glucose level measuring apparatus, a test instrument for providing an enzyme reaction system is attached to the measuring apparatus, and then blood is supplied to the test instrument for the measurement of the blood glucose level. A widely used test instrument for a blood glucose level measuring apparatus may be a biosensor of capillary type which utilizes capillary action for introducing blood to the enzyme reaction system.

FIGS. 16 and 17 illustrate an example of biosensor which utilizes a capillary system. FIG. 16 is an exploded perspective view of the biosensor 90, whereas FIG. 17 is a sectional view of the biosensor 90 in the assembled state, the section being taken along lines XVII-XVII in FIG. 16.

The biosensor 90 includes a substrate 91 on which a spacer 92 and a cover 93 are laminated to define a capillary 94. The capillary 94 is open at a suction port 94a and at a discharge port 94b formed in the cover 93. The substrate 91 is provided with an operative electrode 95, a counterpart electrode 96 and a reagent portion 97. The reagent portion 97 contains oxidoreductase and an electron carrier.

For measuring the blood glucose level using the biosensor 90, blood is introduced via the suction port 94a of the biosensor 90, which is pre-mounted to the blood glucose level measuring apparatus. The blood introduced moves through the capillary 94 to the reagent portion 97 by capillary action and dissolves the reagent portion 97 to form a liquid phase reaction system. By the action of enzyme, the glucose in the blood is oxidized, while the electron carrier is reduced. When certain voltage is applied across the operative electrode 95 and the counterpart electrode 96 contacting the liquid phase reaction system, the reduced electron carrier is oxidized. The blood glucose level measuring apparatus detects the oxidation current and computes the glucose concentration based on the oxidation current.

A typical way to extract blood for introduction into the biosensor 90 may be to use such a lancing apparatus as disclosed in JP-A-9-266898, for example. A lancing apparatus is provided with a needle for puncturing the skin of the user to cause bleeding. By bringing the suction port 94a of the biosensor 90 into contact with the extracted blood, the user can introduce the blood into the capillary 94 through the suction port 94a.

Recently, as disclosed in JP-A-2000-231, for example, a blood glucose level measuring apparatus with a lancing function is proposed. With it, both the lancing of the skin using a lancet (introduction of blood into the biosensor 90) and the measurement of the blood glucose level can be performed.

In using the biosensor 90 mentioned above, the introduction of blood need be performed by bringing the suction port 94a, which is very small, into proper contact with the blood. This operation necessitates the user's visual confirmation. Thus, it is an intolerable burden to introduce blood into the biosensor 90 after bleeding is caused with the use of a lancing apparatus.

In using the blood glucose level measuring apparatus having a lancing function, on the other hand, it is often difficult to visually confirm the bleeding position, which causes the following problems. The first problem is that the blood supply to the biosensor 90 cannot be repeated under the same conditions. The second problem arises when the blood supply is performed by allowing the blood to come into contact with the suction port 94a before a sufficient amount of blood has oozed out. In such a case, the time taken for introducing an amount of blood necessary for the measurement into the capillary 94 depends on the bleeding speed from the skin. Since the bleeding speed varies depending on the bleeding portion and among individuals, the time taken for introducing an amount of blood necessary for the measurement cannot be constant. Further, in the biosensor 90 utilizing the capillary system, the travel speed of the blood through the capillary 94 depends on the viscosity of the blood, which varies among individuals or depending on the physical condition. Therefore, the time taken for blood introduction into the thin capillary 94 varies largely also due to variations of the viscosity of blood.

Such variations of time for blood introduction influence the progress of the enzyme reaction, which starts by the dissolution of the reagent portion 97 in blood. As a result, reliable measurements cannot be obtained. Further, the variations of time for blood introduction often hinders the shortening of the measurement time.

DISCLOSURE OF THE INVENTION

An object of the present invention is to make it possible to properly introduce a necessary amount of sample liquid to the capillary of a test instrument without the need for strict visual confirmation and to perform accurate measurement with high reproducibility.

According to a first aspect of the present invention, there is provided a test instrument comprising a capillary for moving a sample liquid, a liquid pooling portion communicating with the capillary for retaining the sample liquid to be introduced into the capillary, and a liquid introduction selector for selecting whether or not the sample liquid retained in the liquid pooling portion is introduced into the capillary.

The test instrument of the invention may further include a substrate, and a cover for defining the capillary together with the substrate, for example.

The liquid pooling portion may include an introduction port communicating with the capillary for introducing the sample liquid. Preferably, the liquid pooling portion continuously penetrates the substrate and the cover thicknesswise. Preferably, the liquid pooling portion has an internal capacity which is generally equal to or larger than the internal capacity of the capillary.

For example, the introduction port is formed at the substrate or the cover. Preferably, the introduction port opens wider than the entrance of the capillary. With such an arrangement, the sample liquid can be introduced more easily than when the sample liquid is introduced directly into the capillary. Preferably, a close contact layer which is more adherent to skin than the substrate or the cover is provided adjacent the introduction port. The close contact layer may comprise a contacting member fitted in the introduction port. The contacting member may be arranged to cover the periphery or surrounding portion of the introduction port.

For example, the liquid introduction selector includes a discharge port for discharging air from the inside of the capillary. In this case, it is preferable that both of the introduction port and the discharge port are formed at the substrate or the cover. With this structure, when the test instrument is brought into close contact with the skin for introducing blood as the sample liquid, the introduction port and the discharge port can be simultaneously closed with the skin.

Preferably, the test instrument of the present invention further includes a detector for detecting whether or not an intended amount of sample liquid is supplied to the liquid pooling portion.

For example, the detector includes a first detection electrode and a second detection electrode. Preferably, the first electrode and the second electrode are exposed to the inside of the liquid pooling portion at least partially. In this case, whether or not an intended amount of sample liquid is supplied to the liquid pooling portion is determined by detecting whether or not electrical conduction through the sample liquid is provided between the first detection electrode and the second detection electrode.

The test instrument of the present invention includes a first measurement electrode and a second measurement to measure the concentration of a particular component in the sample liquid by an electrochemical method. In this case, a reagent portion is provided in the capillary. The reagent portion is provided in a solid state for dissolution upon supply of the sample liquid to the capillary. The first measurement electrode and the second measurement electrode serve to apply a voltage to the reaction system formed by the reagent portion and the sample liquid when the reagent portion dissolves. Preferably, the first detection electrode is electrically connected to the first measurement electrode, whereas the second detection electrode is electrically connected to the second measurement electrode. In this case, whether or not the sample liquid is supplied can be detected by utilizing the electrical circuit required for the concentration measurement.

According to a second aspect of the present invention, there is provided an attachment for mounting to a concentration measuring apparatus for measuring concentration of a particular component in a sample liquid. The attachment is provided with a test instrument including a capillary for moving the sample liquid. The test instrument includes a liquid pooling portion communicating with the capillary for retaining the sample liquid to be introduced into the capillary, and a liquid introduction selector for selecting whether or not the sample liquid retained in the liquid pooling portion is introduced into the capillary.

For example, the test instrument includes a substrate, and a cover for defining the capillary together with the substrate.

The attachment of the present invention may further comprise a lancet including a lancing needle. Preferably, the liquid pooling portion continuously penetrates the substrate and the cover thicknesswise for allowing the lancing needle to pass through the liquid pooling portion.

For example, the liquid introduction selector may include a discharge port for discharging air from the inside of the capillary. In this case, whether or not the sample liquid retained in the liquid pooling portion is introduced into the capillary is selected by opening or closing the discharge port.

For example, the skin may be utilized for opening and closing of the discharge port. Alternatively, a mechanism for opening and closing the discharge port may be provided in the concentration measuring apparatus.

According to a third aspect of the present invention, there is provided a concentration measuring apparatus for measuring the concentration of a particular component in a sample liquid by utilizing an attachment mounted to the concentration measuring apparatus and provided with a test instrument. The test instrument includes a capillary for moving a sample liquid, a liquid pooling portion communicating with the capillary for retaining the sample liquid to be introduced into the capillary, and a liquid introduction selector for selecting whether or not the sample liquid retained in the liquid pooling portion is introduced into the capillary. The concentration measuring apparatus further includes a selector for selecting whether or not the sample liquid is introduced into the capillary.

The liquid introduction selector may include a discharge port for discharging air from the inside of the capillary. The selector may include an open/close member for opening or closing the discharge port.

When the blood extracted from the skin is directly supplied to the test instrument, the discharge port may be closed or opened by bringing the skin into or out of contact with the discharge port. Specifically, the skin may be brought into or out of contact with the discharge port by appropriately varying the bulging degree of the skin by the concentration measuring apparatus. The bulging degree of the skin may be varied by varying the degree of a negative pressure to be exerted on the skin. To exert a negative pressure on the skin, a negative pressure generator may be provided in the concentration measuring apparatus. In this case, the negative pressure generator constitutes the selector for selecting the liquid introduction to the capillary. The negative pressure generator may be driven electrically or manually.

Preferably, the test instrument includes a detector for detecting whether or not an intended amount of sample liquid is supplied to the liquid pooling portion. In this case, the concentration measuring apparatus further includes a determiner for determining whether or not an intended amount of sample liquid is supplied to the liquid pooling portion by utilizing the detector.

According to a fourth aspect of the present invention, there is provided a concentration measuring apparatus for measuring the concentration of a particular component in a sample liquid by utilizing an attachment mounted to the concentration measuring apparatus and provided with a test instrument. The test instrument includes a capillary for moving a sample liquid, a liquid pooling portion communicating with the capillary for retaining the sample liquid to be introduced into the capillary, and a detector for detecting whether or not an intended amount of sample liquid is supplied to the liquid pooling portion. The concentration measuring apparatus further includes a determiner for determining whether or not an intended amount of sample liquid is supplied to the liquid pooling portion by utilizing the detector.

BEST MODE FOR CARRYING OUT THE INVENTION

Preferred embodiments of the present invention will be described below with reference to the accompanying drawings. Specifically, a biosensor for measuring a blood glucose level, an attachment and a blood glucose level measuring apparatus will be described below.

First, a first embodiment of the present invention will be described.

Figure 1:
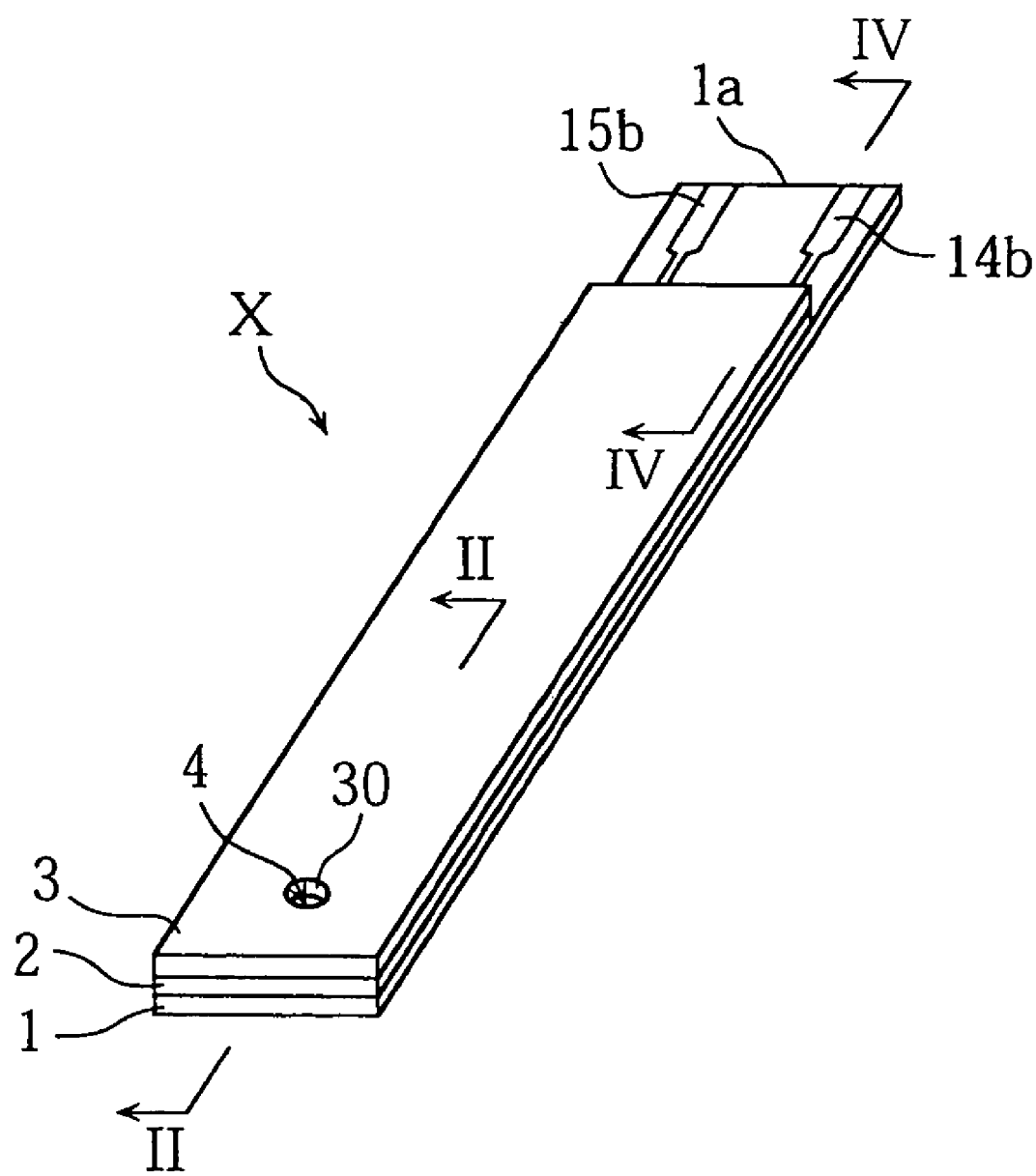
FIG. 1 is a perspective view illustrating an example of biosensor according to a first embodiment of the present invention.
Figure 2:
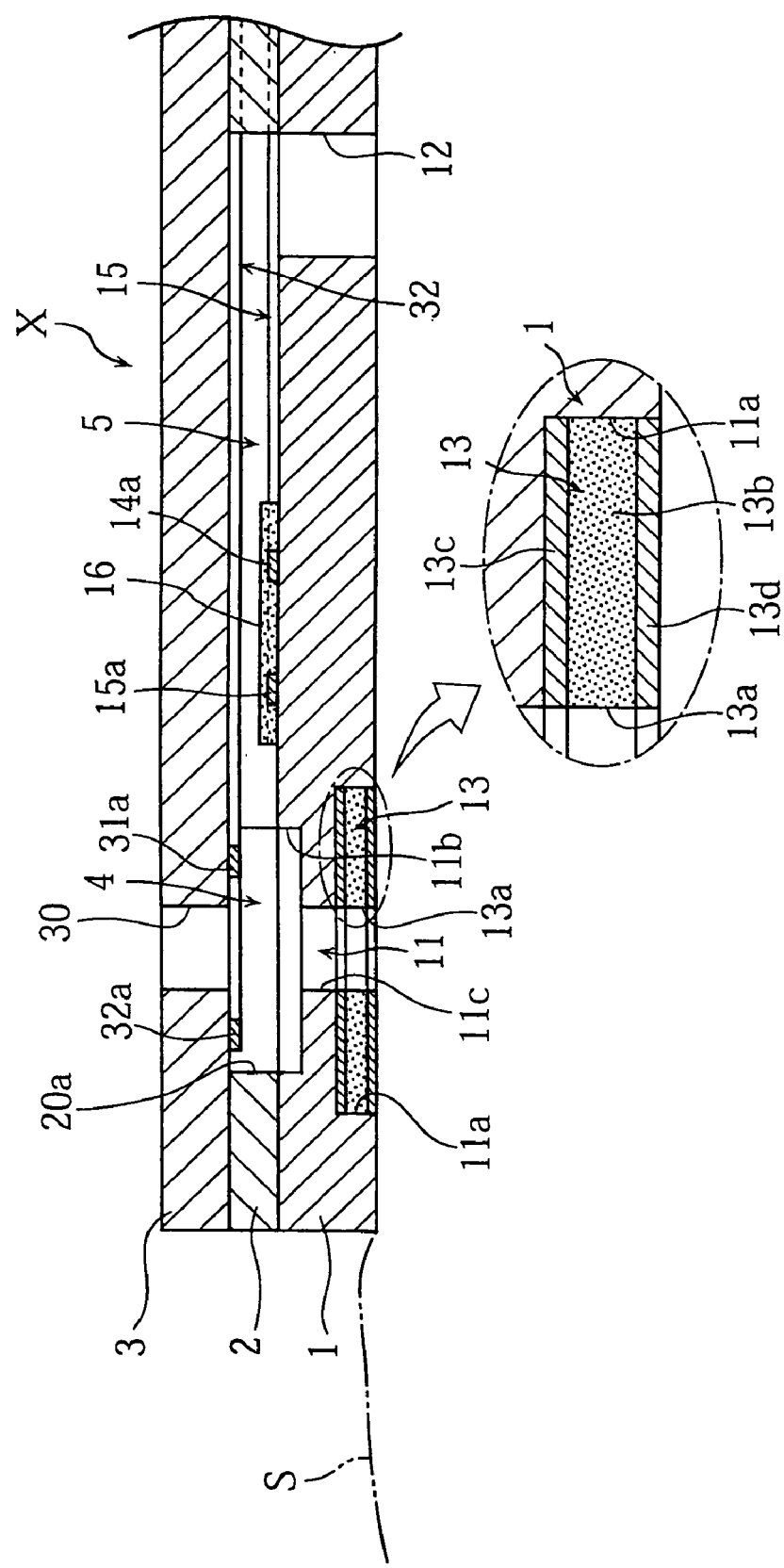
FIG. 2 is a sectional view taken along lines II-II in FIG. 1.

FIGS. 1 and 2 show a disposable biosensor X, which is mounted in use to a blood glucose level measuring apparatus. The biosensor X includes a substrate 1 on which a cover 3 is laminated via a spacer 2, thereby defining a liquid pooling portion 4 and a capillary 5.

Figure 3:
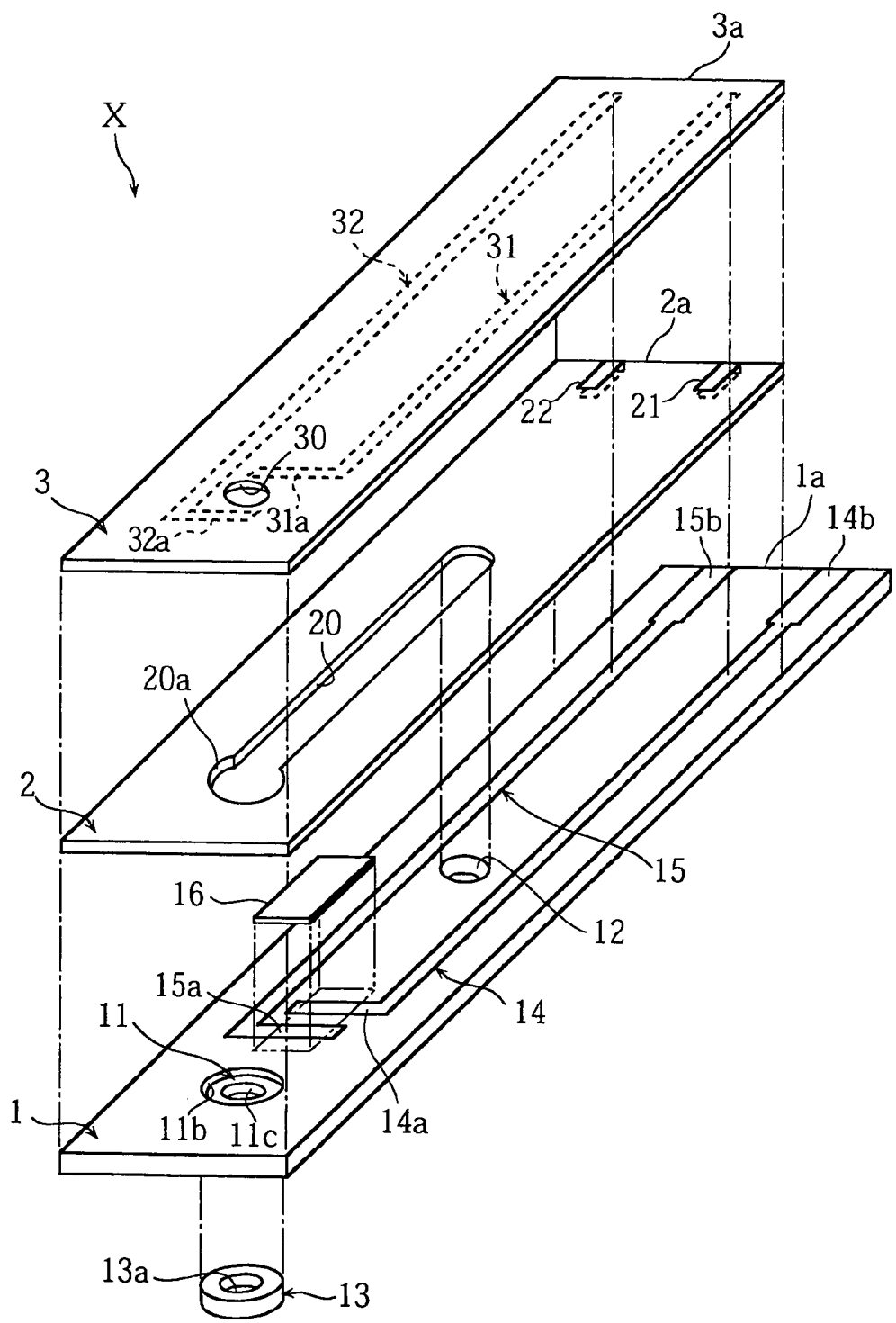
FIG. 3 is an exploded perspective view of the biosensor shown in FIG. 1.

As shown in FIGS. 2 and 3, the substrate 1 is formed with a first through-hole 11 and a second through-hole 12. The first through-hole 11 constitutes part of the liquid pooling portion 14 and also serves as an inlet for introducing a sample liquid such as blood to the liquid pooling portion 4. The second through-hole 12 serves to discharge air from the inside of the capillary 5.

The first through-hole 11 comprises a first circular recess 11a, a second circular recess 11b, and a penetrating portion 11c which connects the two circular recesses to each other and which is smaller in diameter than the circular recesses 11a and 11b. In the first circular recess 11a, a contacting member 13 is fitted.

The contacting member 13 has an annular configuration with a central through-hole 13a and has a thickness of about 70 μm. The contacting member 13 has an outer diameter corresponding to the outer diameter of the first circular recess 11a and an inner diameter (the diameter of the through-hole 13a) corresponding to the diameter of the penetrating portion 11c. As clearly shown in FIG. 2, the contacting member 13 comprises a water absorbing layer 13b sandwiched between a pair of adhesive layers 13c and 13d. The water absorbing layer 13b is a thin film having a thickness of about 50 μm and made of nonwoven fabric, for example. The adhesive layers 13c and 13d have adhesion appropriate for close contact with the skin. The adhesive layer 13c of the contacting member 13 is bonded to the substrate 1. The adhesive layer 13d has an obverse surface which is generally flush with the lower surface of the substrate 1. In measuring a blood glucose level, the adhesive layer 13d of the contacting member 13 contacts the skin S of the user so that blood once retained in the liquid pooling portion 4 does not leak to the outside.

The contacting member 13 described above is fitted in the first circular recess 11a formed in the substrate 1. However, the first circular recess 11a may be dispensed with, and the contacting member 13 may be bonded to the lower surface of the substrate 1. Further, instead of the above-described structure, the contacting member may be made of a sufficiently resilient material such as silicone rubber.

Figure 4:
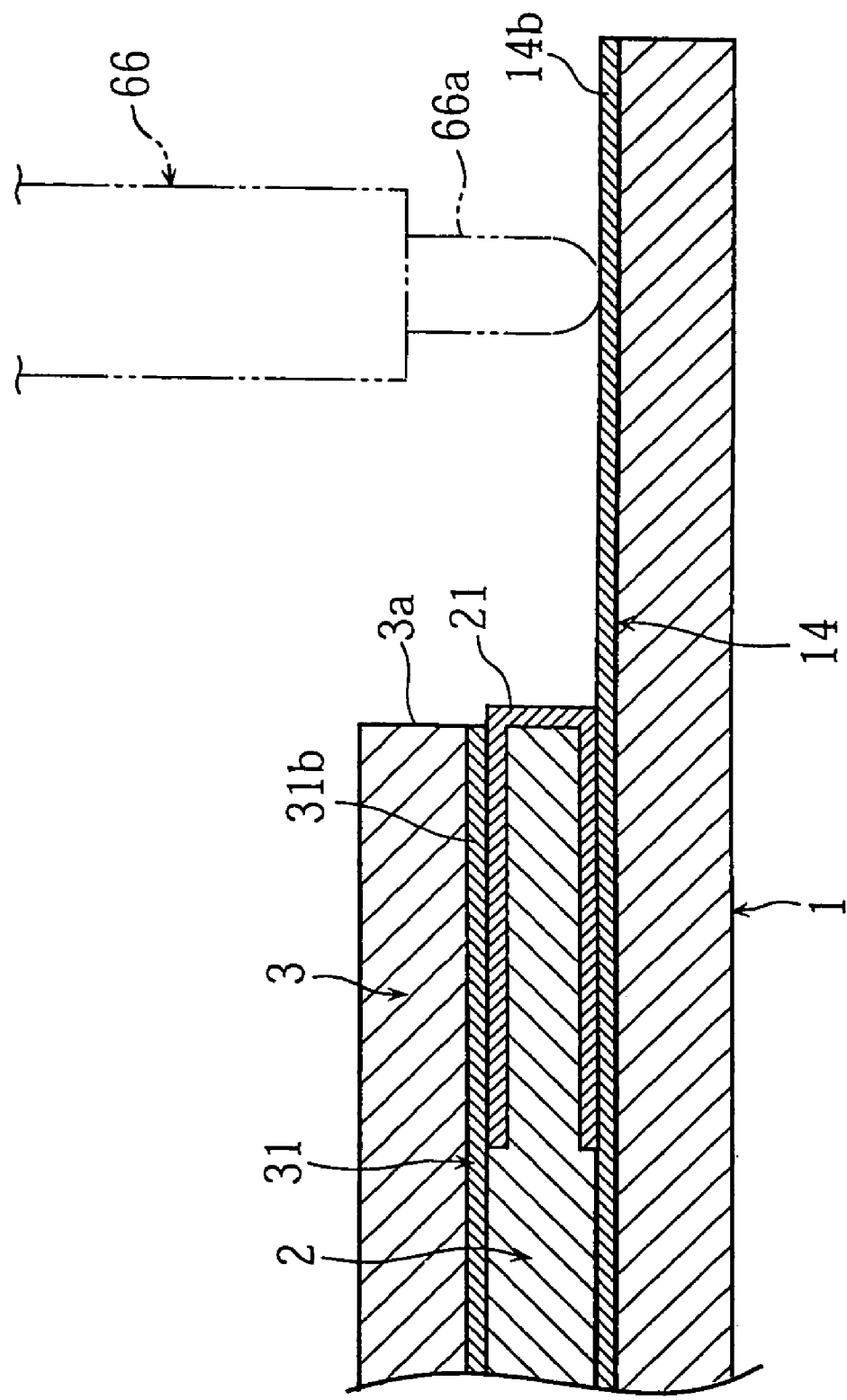
FIG. 4 is a sectional view taken along lines IV-IV in FIG. 1.

As shown in FIG. 3, the insulating substrate 1 has an upper surface formed with an operative electrode 14, a counterpart electrode 15, and a reagent portion 16 connecting these electrodes to each other. The operative electrode 14 and the counterpart electrode 15 extend from an end edge 1a of the substrate 1 longitudinally of the substrate 1. The operative electrode 14 and the counterpart electrode 15 have respective first ends 14a and 15a extending widthwise of the substrate 1 and facing the interior of the capillary 5, as clearly shown in FIG. 2. In measuring the blood glucose level, the voltage provided between the first ends 14a and 15a of the electrodes 14 and 15 is applied to the sample liquid. As shown in FIGS. 1 and 3, the operative electrode 14 and the counterpart electrode 15 respectively have second ends as terminals 14b and 15b. As shown in FIG. 4, the terminals are provided for electrical connection with terminals 66a of the blood glucose level measuring apparatus.

The reagent portion 16 shown in FIGS. 2 and 3 is in a solid state and contains oxidoreductase and an electron carrier. As clearly shown in FIG. 2, the reagent portion 16 is arranged in the capillary 5 and kept in contact with the first ends 14a and 15a of the operative electrode 14 and the counterpart electrode 15. As oxidoreductase, use may be made of glucose oxidase which oxidizes glucose in blood to gluconic acid while reducing the electron carrier. As the electron carrier, use may be made of potassium ferricyanide, for example.

The spacer 2 has an elongated rectangular configuration which is slightly shorter than the substrate 1. The spacer 2 is formed with a slit 20 communicating with the first and the second through-holes 11 and 12 of the substrate 1. The slit 20 has an end 20a located directly above the first through-hole 11 of the substrate 1. As shown in FIG. 3, the spacer 2 has an end edge 2a provided with a pair of conductive portions 21 and 22. As shown in FIGS. 3 and 4, the conductive portions 21 and 22, having electric conductivity, extend continuously on an upper surface, a side surface and a lower surface of the spacer 2.

As shown in FIG. 3, the cover 3 has an elongated rectangular configuration which is generally equal in size to the spacer 2. As clearly shown in FIG. 2, the cover 3 is formed with a through-hole 30 located directly above the first through-hole 11 of the substrate 1. The through-hole 30 constitutes part of the liquid pooling portion 4. The through-hole 30 is provided for passing a lancing needle of a lancet provided at the blood glucose level measuring apparatus, which will be described later. Further, in introducing blood to the liquid pooling portion 4., the through-hole 30 is utilized for discharging air from the inside of the liquid pooling portion 4.

As shown in FIGS. 2 and 3, the cover 3 has a lower surface provided with a pair of detection electrodes 31 and 32. As clearly shown in FIG. 2, the detection electrodes 31 and 32 have respective ends 31a and 32a exposed to the liquid pooling portion 4. Each of the detection electrodes 31 and 32 extends from a portion adjacent the through-hole 30 to an end edge 3a of the cover 3.

As shown in FIG. 4, the detection electrode 31 is electrically connected to the conductive portion 21 of the spacer 2 at the end edge 3a of the cover 3. The conductive portion 21 is electrically connected to the operative electrode 14 provided on the substrate 1. The electrical connection between the conductive portion 21, the detection electrode 31 and the operative electrode 14 is provided using a conductive adhesive, for example. Though not illustrated, the detection electrode 32 is connected to the counterpart electrode 15 via the conductive portion 22. Therefore, it is possible to detect whether or not an electrical connection (liquid junction) is established between the detection electrodes 31 and 32 by utilizing the terminals 14a and 15a of the operative electrode 14 and the counterpart electrode 15.

Referring to FIG. 2, the liquid pooling portion 4 serves to temporarily retain blood to be supplied to the capillary 5. The liquid pooling portion 4 is made up of the first through-hole 11 of the substrate 1, the end 20a of the slit 20 of the spacer 2, and the through-hole 30 of the cover 3. Thus, the liquid pooling portion 4 penetrates thicknesswise of the biosensor X to open upward and downward. The liquid pooling portion 4 may have an internal capacity of 1.5-2.5 μL, for example.

The first circular recess la of the liquid pooling portion 4 and the through-hole 13a of the contacting member 13 are open wider than the inlet to the capillary 5. Therefore, introduction of blood to the biosensor X can be performed more easily and reliably than when the blood is introduced directly to the capillary 5.

As noted above, the capillary 5 communicates with the second through-hole 12 of the substrate 1 and the liquid pooling portion 4. After the blood retained in the liquid pooling portion 4 is sucked into the capillary 5, the blood can be held in the capillary. The capillary 5 has an internal capacity which is smaller than that of the liquid pooling portion 4. Specifically, the internal capacity may be 0.9-1.0 μL, for example.

Preferably, surfaces defining the liquid pooling portion 4 and the capillary 5 are subjected to hydrophilic treatment to be highly hydrophilic for realizing smooth supply of the sample liquid. As the hydrophilic treatment, a film of Vinylon may be provided or a surface-active agent may be coated.

In the biosensor X, the sample liquid supplied to the liquid pooling portion 4 can be guided to the capillary 5 by capillary action. The sample liquid guided to the capillary 5 dissolves the reagent portion 16 to form a liquid phase reaction system in the capillary 5. At that time, by the action of oxidoreductase, a particular component in the sample liquid loses electrons and is oxidized, and the electrons are supplied to the electron carrier to reduce the electron carrier. When a voltage is applied across the operative electrode 14 and the counterpart electrode 15, the electrons transferred to the electron carrier are released, whereby redox current flows.

Figure 5:
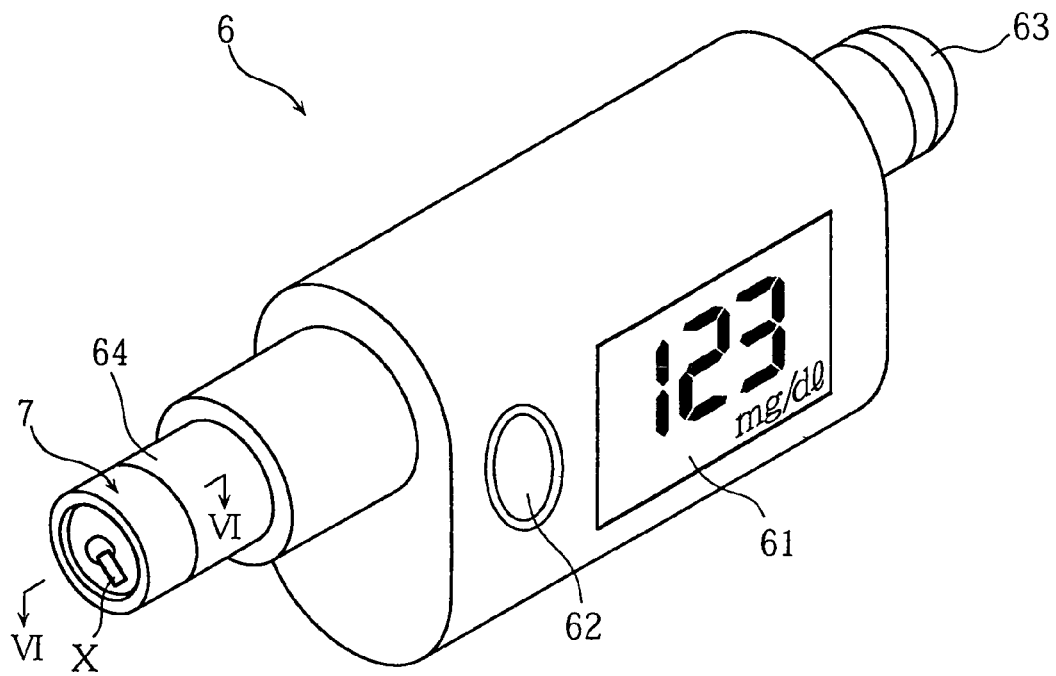
FIG. 5 is a perspective view illustrating a concentration measuring apparatus according to a first embodiment of the present invention.

FIG. 5 illustrates a blood glucose level measuring apparatus 6, which is used with an attachment 7 mounted thereto and has a lancing (blood drawing) function and a blood glucose level measuring function. The blood glucose level measuring apparatus 6 includes a display 61, an operation switch 62, a press switch 63 and a mount portion 64.

The display 61, which is provided for displaying e.g. measurement results, may comprise a liquid crystal display or an LED display. The operation switch 62 is pressed in starting a series of process steps for the blood glucose level measurement, for example. The press switch 63 is pressed in stating the lancing operation. The mount portion 64 is a portion for mounting the attachment 7.

Figure 6:
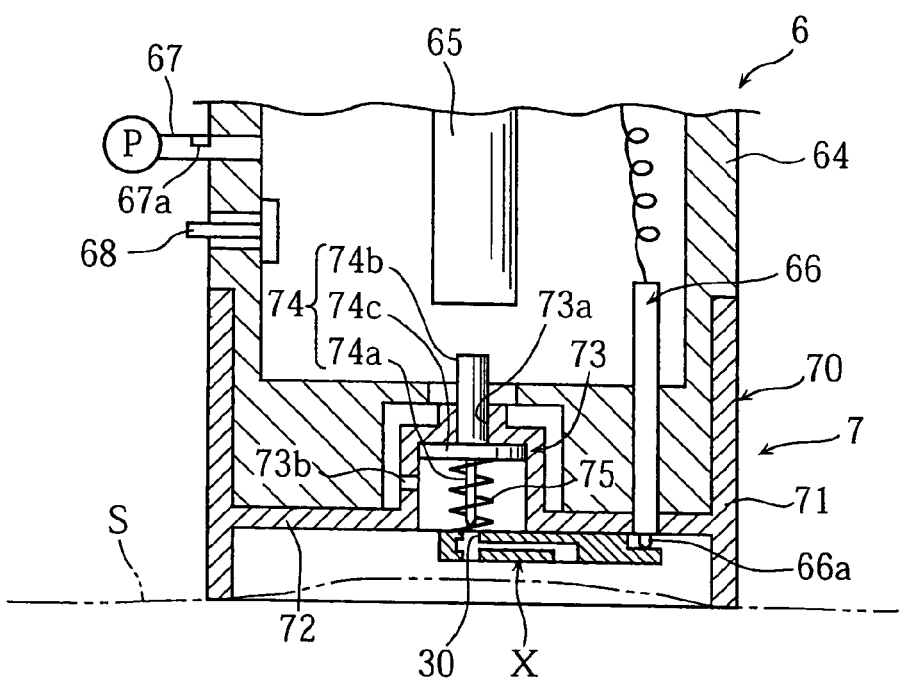
FIG. 6 is a sectional view taken along lines VI-VI in FIG. 5.

As shown in FIG. 6, the attachment 7 is made up of the above-described biosensor X and a main body 70. The main body 70 includes a cylindrical portion 71 and a bottom wall 72. The cylindrical portion 71 is fitted around a front end of the mount portion 64. The bottom wall 72 has a projection 73 bulging upward. The projection 73 serves to hold a lancet 74 provided with a lancing needle 74a, and the opening of the projection is covered with the biosensor X attached to the bottom wall 72. The projection 73 has an upper wall formed with a thorough-hole 73a for passing a push portion 74b of the lancet 74. The projection 73 has a circumferential wall formed with a through-hole 73b for allowing air movement in e.g. driving a pump P, as will be described later. The projection 73 accommodates a coil spring 75 arranged, in a compressed state, between a flange 74c of the lancet 74 and the biosensor X. Thus, the lancet 74 is held with the flange 74c pressed against the bottom wall of the projection 73 by the coil spring 75.

The blood glucose level measuring apparatus 6 further includes a pushing rod 65 and a pair of connectors 66 (only one of which is shown in the figure). When the press switch 63 is pressed, the pushing rod 65 is driven to move toward the front end of the apparatus. The pushing rod 65 may be driven by a known latch mechanism or a mechanism utilizing an electromagnet. Each of the connectors 66 is connected to an electric circuit not shown and provided with a connector pin 66a reciprocally movable upward and downward. When the attachment 7 is mounted to the blood glucose level measuring apparatus 6, the connector pins 66a come into contact with the terminals 14b and 15b of the biosensor X, respectively.

A pump P is connected to the mount portion 64 via a connection pipe 67 communicating with the inside of the mount portion. The connection pipe 67 is provided with a pressure sensor 67a for measuring the internal pressure of the mount portion 64. The pump P serves to discharge gas from the inside of the mount portion 64 to depressurize the inside of the cylindrical member 64. The pump P may be incorporated in the blood glucose level measuring apparatus 6 or may be provided outside the blood glucose level measuring apparatus 6. The pump P may be electrically driven or manually driven. In the present embodiment, an electrically driven pump is used.

The mount portion 64 is provided with a relief valve 68. The relief valve 69 is provided for taking in air from the outside to return the pressure in the mount portion 64 to the atmospheric pressure. The relief valve 68 may be a solenoid valve, for example. Alternatively, the relief valve 68 may be opened manually.

Figure 7:
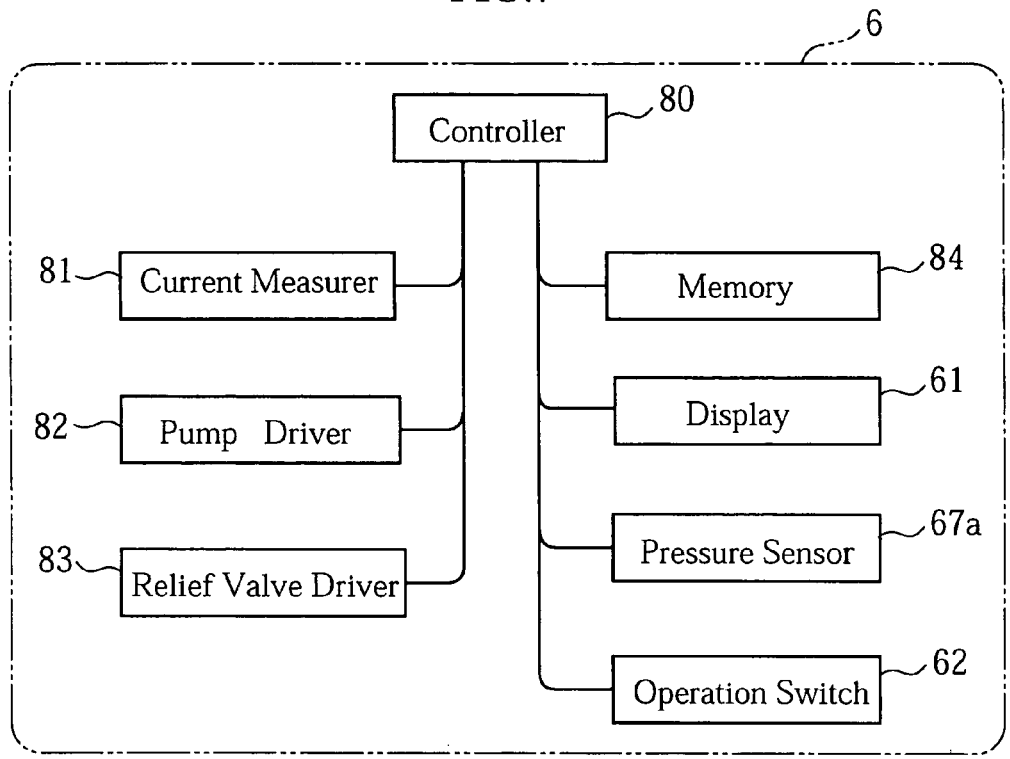
FIG. 7 is a block diagram of the concentration measuring apparatus shown in FIG. 5.

FIG. 7 is a schematic block diagram of the blood glucose level measuring apparatus 6. The blood glucose measuring apparatus 6 includes a controller 80, a current measurer 81, a pump driver 82, a relief valve driver 83 and a memory 84 in addition to the above-mentioned display 61, operation switch 62 and pressure sensor 67a.

The controller 80 serves to control operations of the parts 61, 62, 67a and 81-84 and may comprise a CPU, for example.

The current measurer 81 applies a voltage across the operative electrode 14 and the counterpart electrode 15 of the biosensor X to measure the current flowing through the reagent portion 16. When the attachment 7 is mounted to the mount portion 64, the current measurer 83 is electrically connected to the operative electrode 14 and the counterpart electrode 15 of the biosensor X through the paired connectors 66.

The pump 82 drives the pump P based on instructions from the controller 80. The relief valve driver 83 drives the relief valve 68 based on instructions from the controller 80.

The memory 84, which may comprise a ROM and a RAM, stores programs necessary for the control by the controller 80 and calibration curve data. The memory 84 also serves to temporarily store necessary information in executing a program. The calibration curve data store may represent the relationship between the glucose concentration and the voltage converted from a measured current. The calibration curve data is stored in the form of a formula or a lookup table.

The blood glucose level measuring operation using the blood glucose level measuring apparatus 6 and the attachment 7 will be described below. First, with the attachment 7 mounted to the blood glucose level measuring apparatus 6, the front end of the attachment 7 is pressed against the skin S of an appropriate portion such as an arm or a finger of the user, as shown in FIG. 6. Thus, the opening at the front end of the attachment 7 is closed with the skin S.

Figure 8:
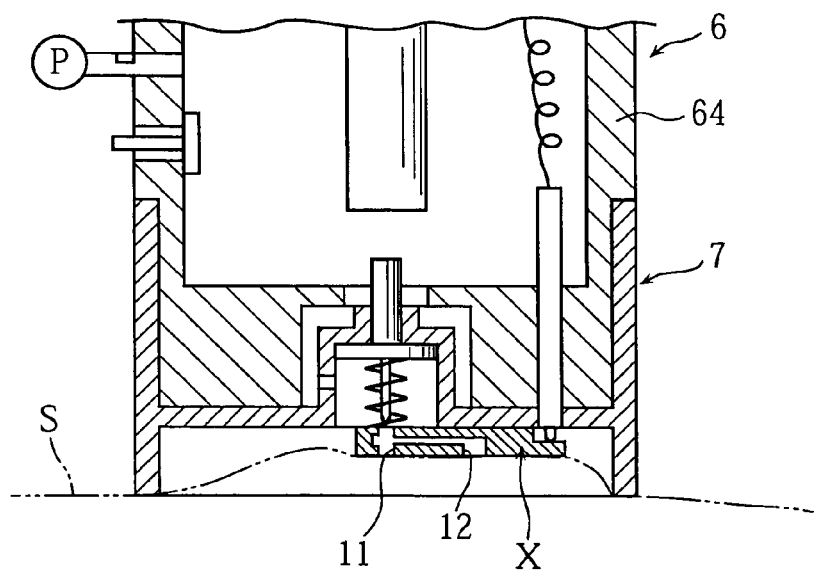
FIG. 8 is a sectional view corresponding to FIG. 6 for describing the lancing operation.

Subsequently, the operation switch 62 of the blood glucose level measuring apparatus 6 is pressed. By this operation, the controller 80 sends a control signal to the pump driver 82 to drive the pump P. As a result, the internal pressure of the mount portion 64 and the attachment 7 reduces gradually. During this operation, the controller 80 continues to monitor the output value from the pressure sensor 67a. The skin S gradually bulges in accordance with the pressure drop to eventually come into contact with the biosensor X, as shown in FIG. 8. As a result, the first through-hole 11 and the second through-hole 12 of the biosensor X are closed with the skin S.

When the pressure sensor 67a detects the predetermined pressure value at which the skin S bulges sufficiently for close contact with the biosensor X, the driving of the pump P is stopped, thereby finishing the depressurization. A message of the finishing of the depressurization may be displayed at the display 61, for example.

Figure 9:
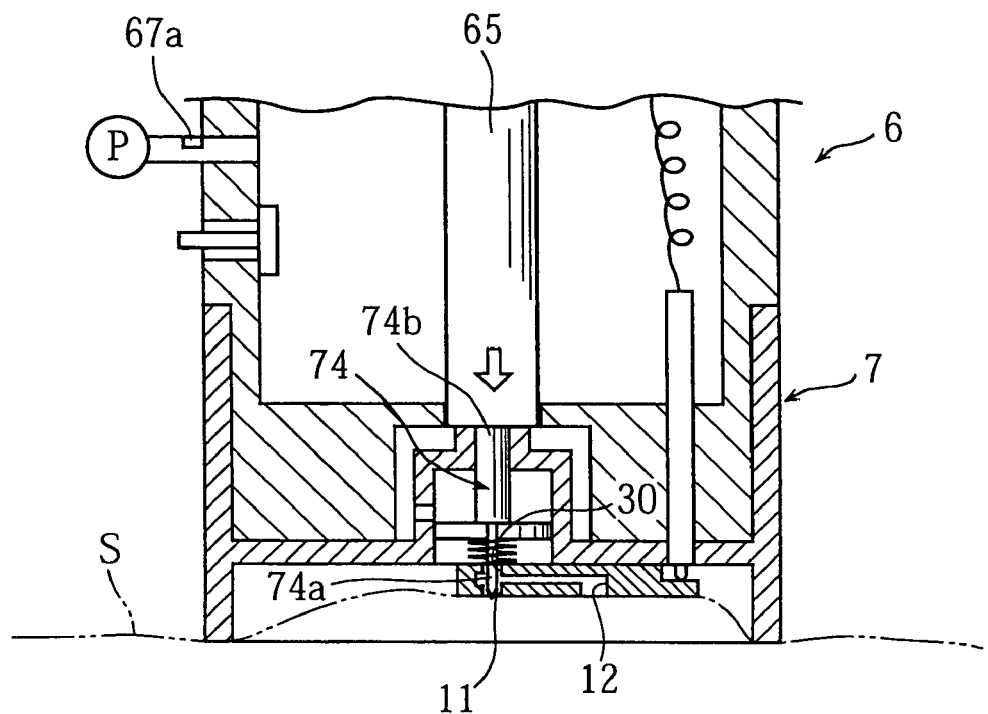
FIG. 9 is a sectional view corresponding to FIG. 6 for describing the lancing operation.

Then, the user presses the press switch 63 of the blood glucose level measuring apparatus 6, which moves the pushing rod 65 swiftly. This pressing operation of the press switch 63 can be performed after the user confirms the finish of the depressurization by referring to the message on the display 61. By this operation, the pushing rod 65 comes into contact with the push portion 74b of the lancet 74 to push the lancet 74 toward the skin S. As a result, the lancing needle 74a of the lancet 74 passes through the through-hole 30, the liquid pooling portion 4 and the first through-hole 11 of the biosensor X to lance the skin S, as shown in FIG. 9. Instead of the above-described structure, the lancing needle 74a may automatically lance the skin S after several seconds have elapsed from the starting of the depressurization by the pump P.

Figure 10:
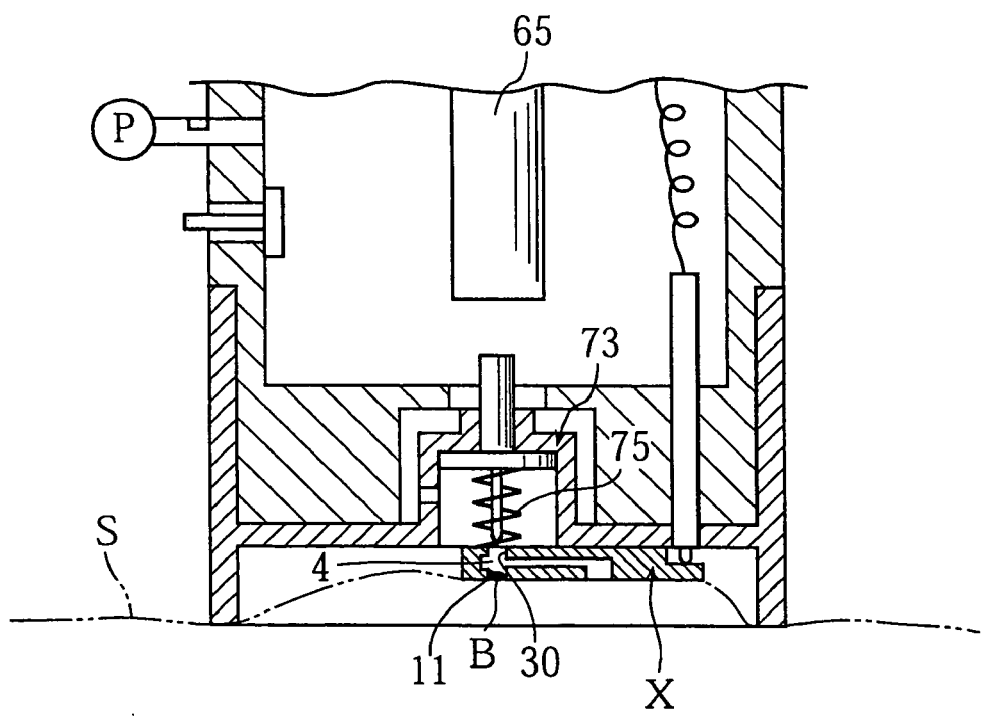
FIG. 10 is a sectional view corresponding to FIG. 6 for describing the lancing operation.
Figure 11:
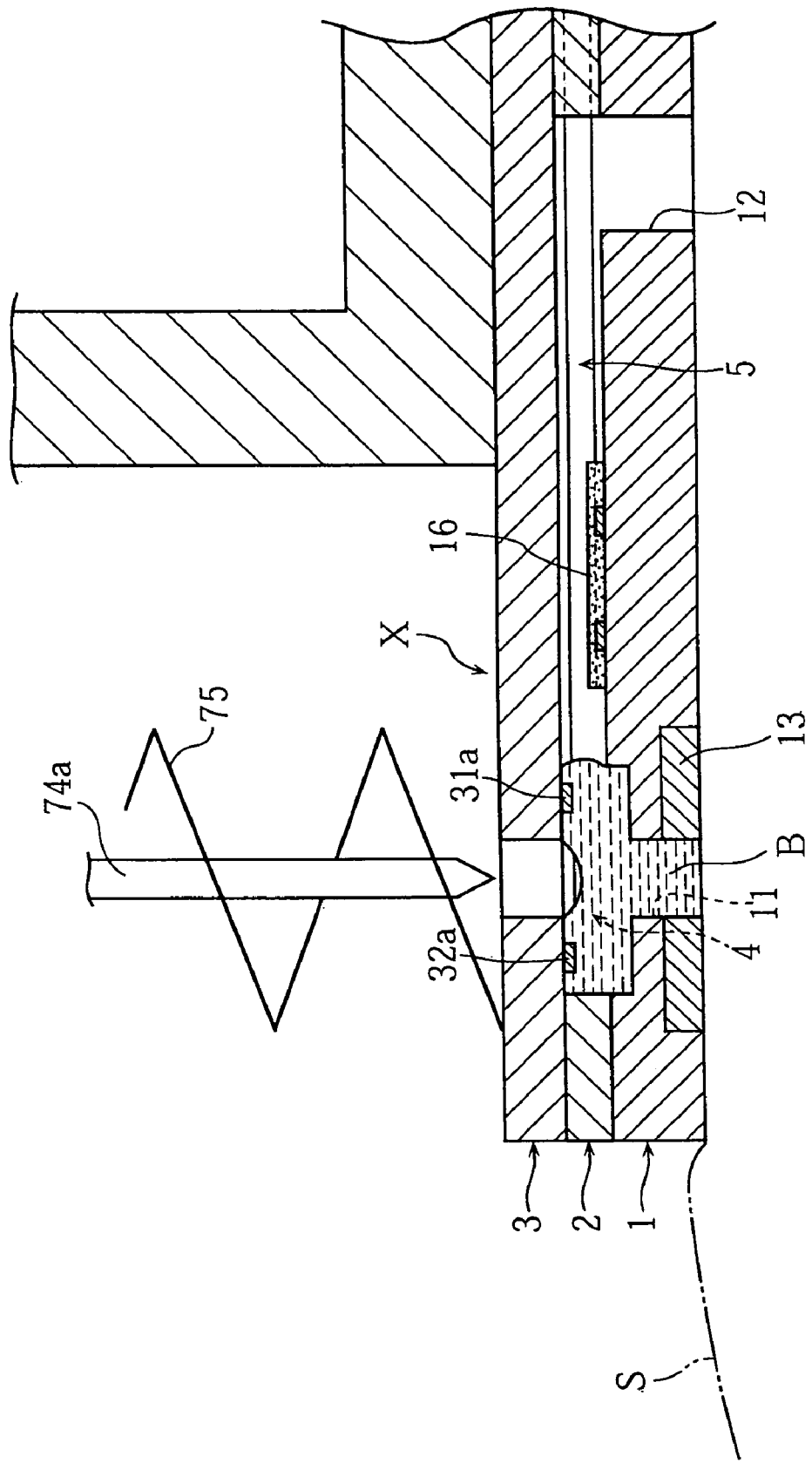
FIG. 11 is an enlarged sectional view illustrating a principal portion of FIG. 10.

Subsequently, as shown in FIG. 10, the rod 65 returns to its original position due to e.g. a resilient force of a spring not shown. The lancing needle 74a returns to its original position due to a resilient force of the spring 75 and is pulled out from the skin S. Blood B bleeds from the skin S appropriately lanced by the lancing needle 74a. As shown in FIG. 11, the lanced portion faces the liquid pooling portion 4, so that the blood extracted from the skin S is immediately introduced into the liquid pooling portion 4 and retained in the liquid pooling portion 4. Since the first through-hole 11 is closed with the skin S, the blood retained in the liquid pooling portion 4 is prevented from leaking to the outside.

Figure 12:
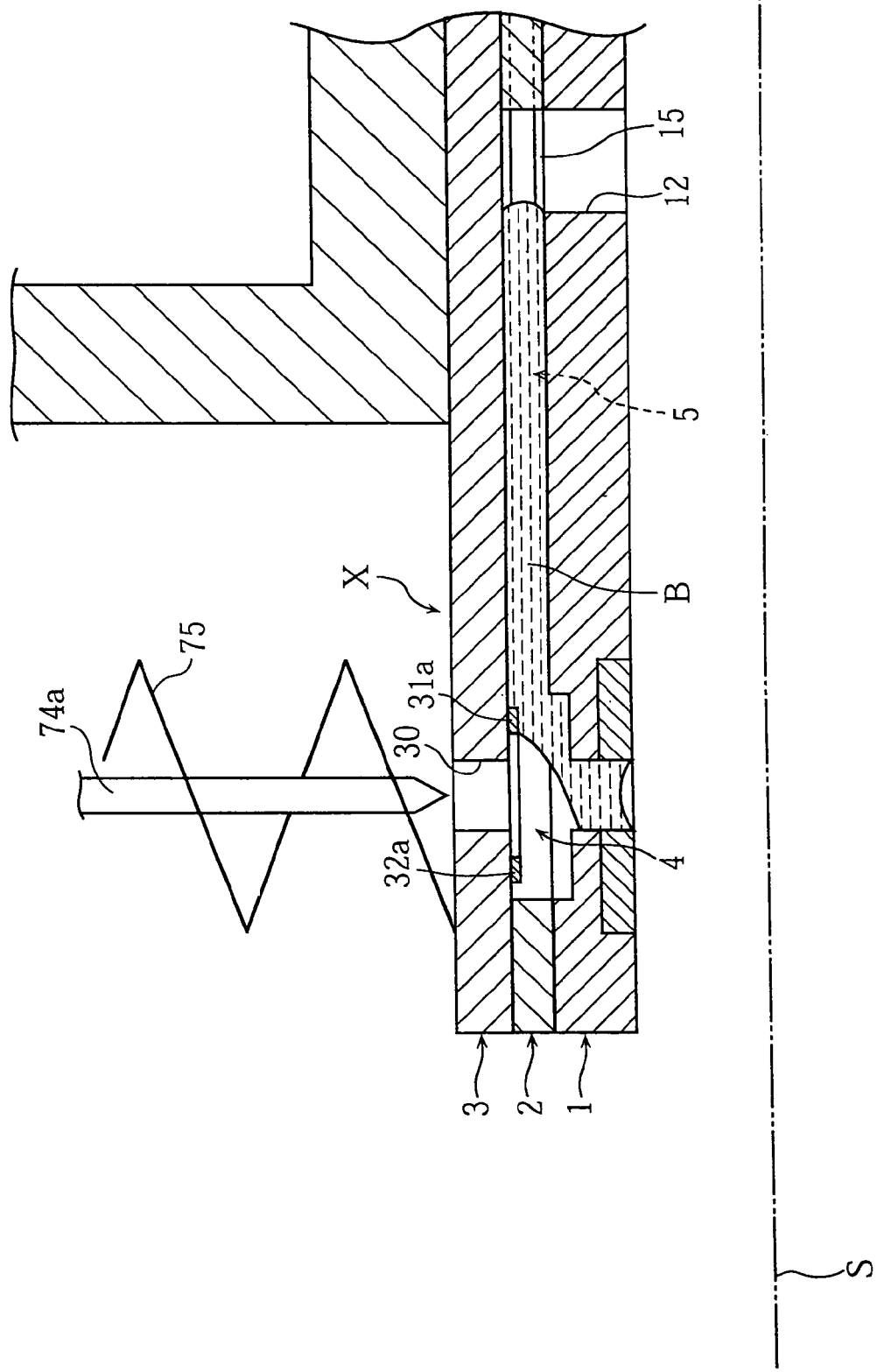
FIG. 12 is an enlarged sectional view corresponding to FIG. 11 for describing the operation of introducing blood into the biosensor.

When an intended amount of blood B is stored in the liquid pooling portion 4, electrical conduction through the liquid is provided between the ends 31a and 32a of the paired detection electrodes 31 and 32 exposed to the liquid pooling portion 4. The electrical conduction is detected by the controller 80 (See FIG. 7) through the detection electrodes 31, 32 and the connector pins 66a. When the controller 80 detects the electrical conduction between the detection electrodes 31 and 32, the relief valve 68 is opened based on instructions from the controller 80. By this operation, the interior of the attachment 7 is exposed to the atmosphere (See FIGS. 7 and 8), whereby the internal pressure of the mount portion 64 (See FIG. 6) returns to the atmospheric pressure. As a result, bulging of the skin S disappears so that the first through-hole 11 and the second through-hole 12 of the biosensor X are opened, as shown in FIG. 12. The return to the atmospheric pressure may be initiated by the user's removal of the attachment 7 from the skin S.

When the second through-hole 12 is opened, the blood B retained in the liquid pooling portion 4 is quickly introduced into the capillary 5 by capillary action. In this way, in the biosensor X, the blood B quickly flows into the capillary 5 after an intended amount of the blood B is stored in the liquid pooling portion 4. Therefore, the time taken for blood introduction in the blood glucose level measurement can be prevented from varying largely depending on e.g. the viscosity of the blood B.

The blood B introduced into the capillary 5 dissolves the reagent portion 16 to form a liquid phase reaction system in the capillary 5. The glucose contained in the blood B is oxidized by the action of oxidoreductase contained in the reagent portion 16. The electrons removed from glucose by this reaction are transferred to the electron carrier via enzyme. Specifically, the electron carrier is reduced by enzyme. Thereafter, when a predetermined voltage is applied across the operative electrode 14 and the counterpart electrode 15 (See FIG. 4), oxidation current flows through the liquid phase reaction system. The current measurer 81 measures the oxidation current. The controller 80 computes the glucose concentration based on the oxidation current, and the calibration curve and computation program stored in the memory 84 (See FIG. 7).

The computation result obtained by the controller 80 is displayed at the display 61 for notifying the user (See FIGS. 5 and 7). The biosensor X and the lancet 74 after use are removed from the blood glucose level measuring apparatus 6 by the user's detachment of the attachment 7 from the blood glucose level measuring apparatus 6.

Next, a second embodiment of the present invention will be described with reference to FIGS. 13 through 15. In these figures, parts or elements which are identical to those of the first embodiment are designated by the same reference signs as those used for the first embodiment, and detailed description thereof will be omitted.

Figure 13:
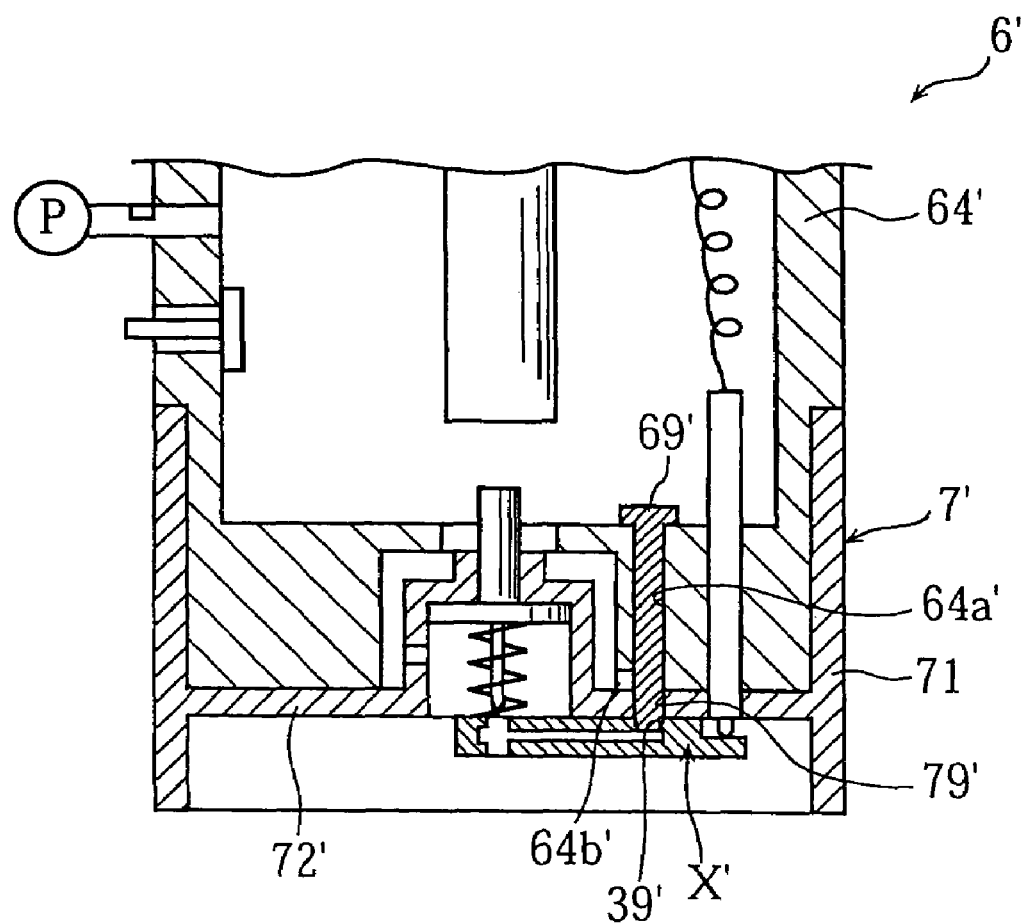
FIG. 13 is a sectional view taken along lines VII-VII in FIG. 5, illustrating a concentration measuring apparatus according to a second embodiment of the present invention.
Figure 14:
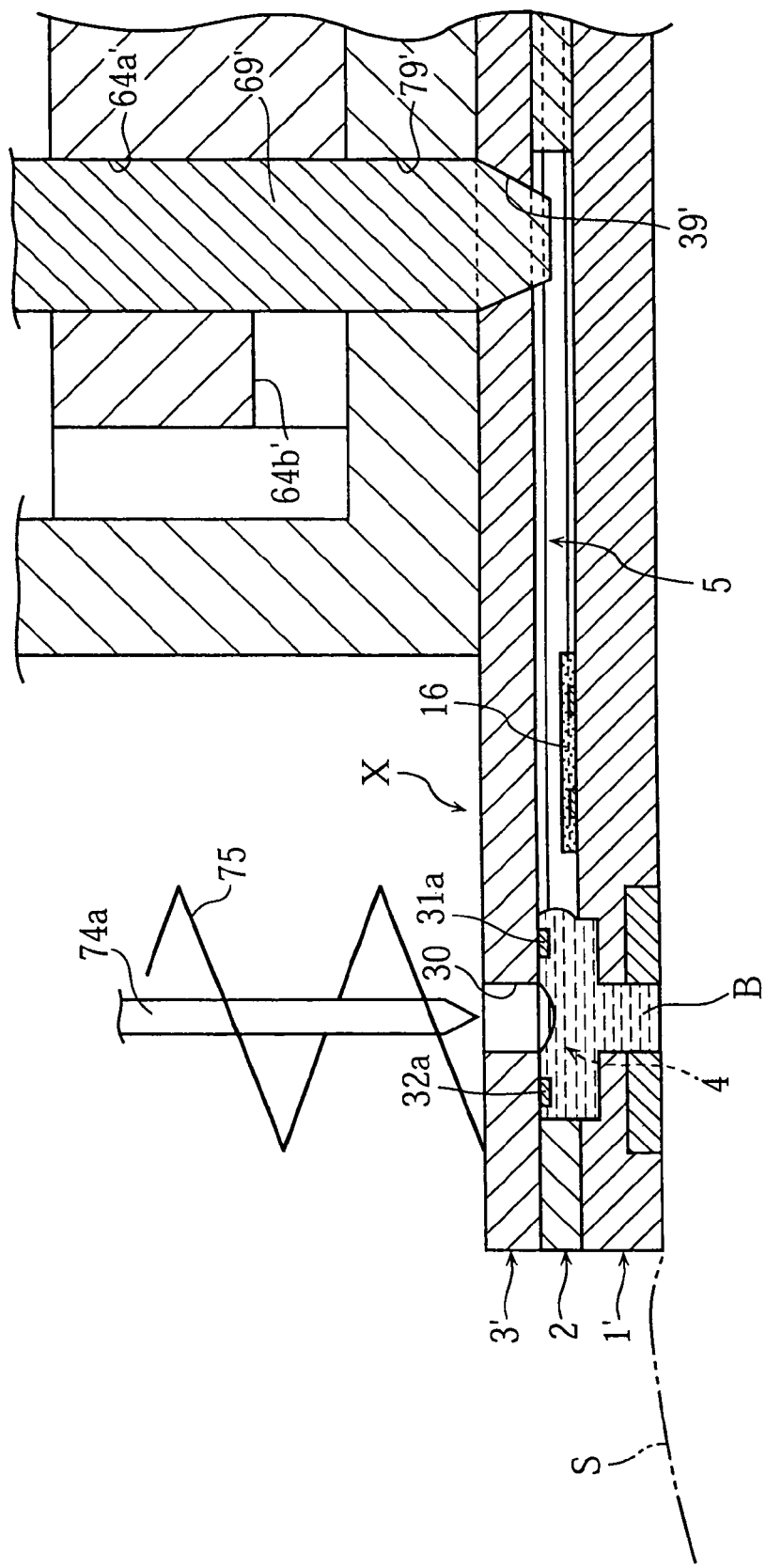
FIG. 14 is an enlarged sectional view illustrating a principal portion of FIG. 13.
Figure 15:
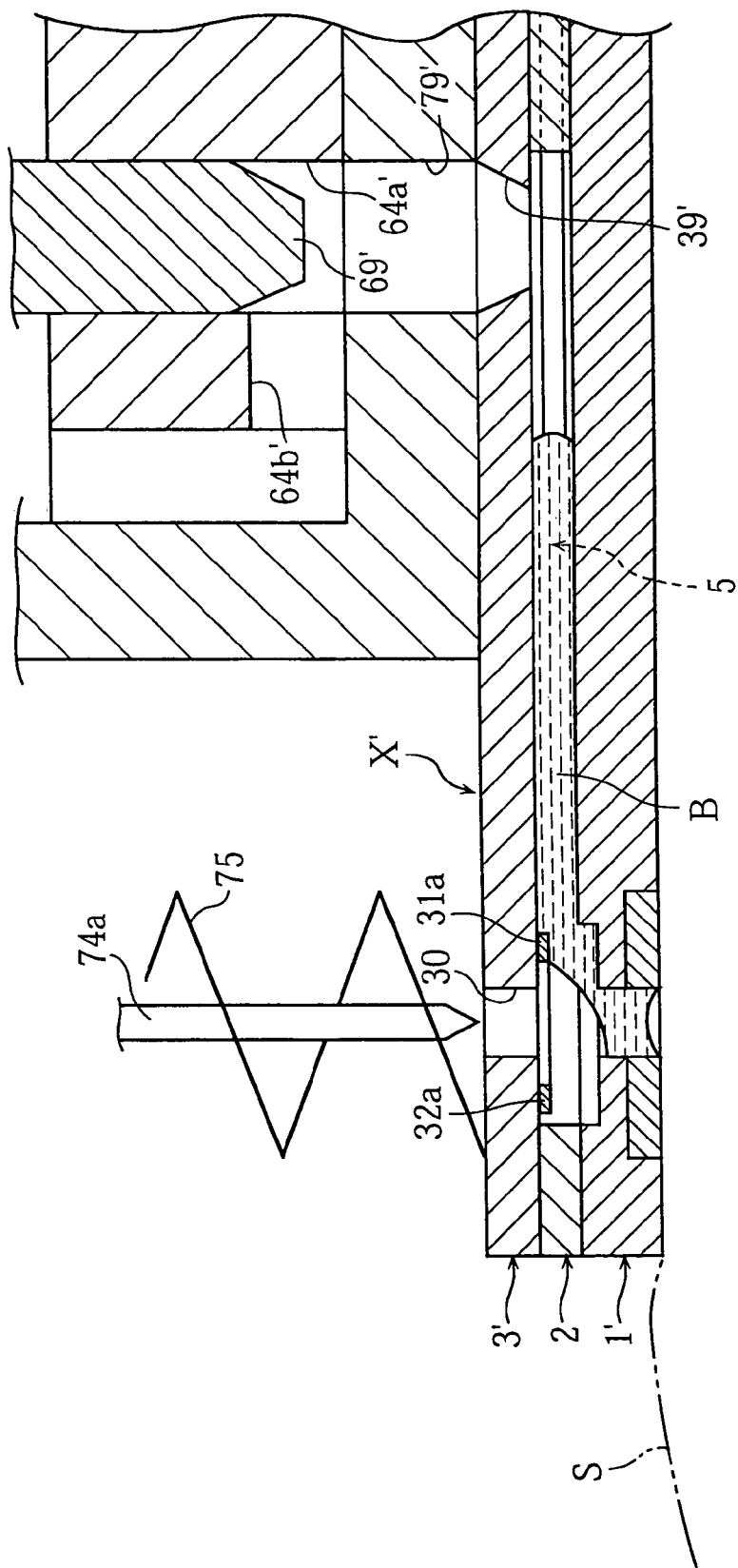
FIG. 15 is an enlarged sectional view corresponding to FIG. 14 for describing the operation of introducing blood into the biosensor.
Figure 16:
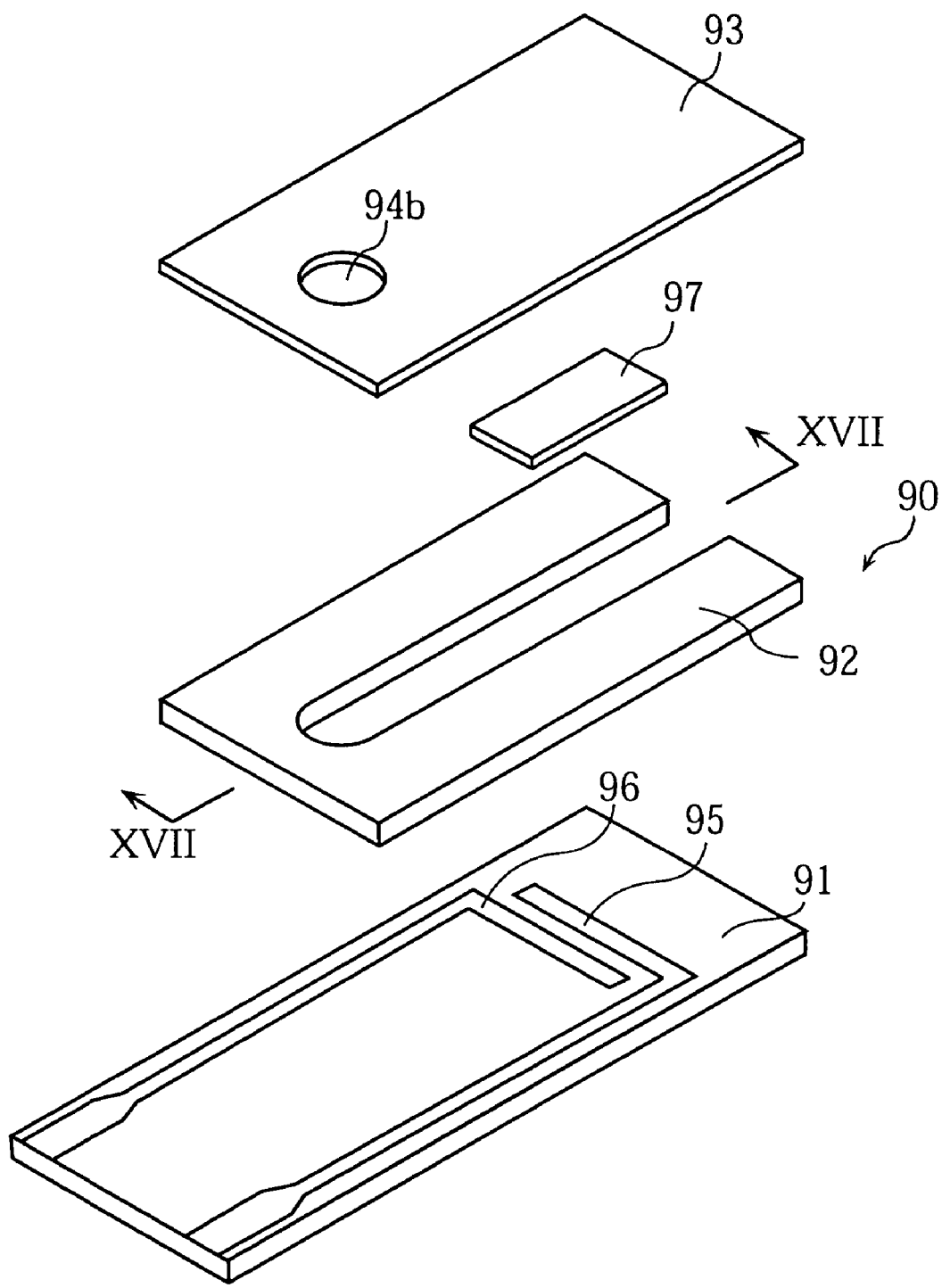
FIG. 16 is an exploded perspective view illustrating a prior art biosensor 90.
Figure 17:
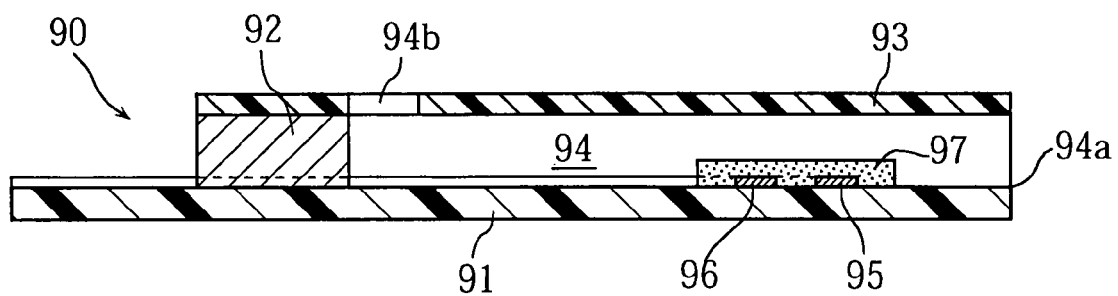
FIG. 17 is a sectional view of the prior art biosensor in an assembled state, which is taken along lines XVII-XVII in FIG. 16.

As shown in FIGS. 13 and 14, in the biosensor X' in this embodiment, an air vent 39' for discharging air from the inside of the capillary 5 is provided in the cover 3', not in the substrate 1'. The air vent hole 39' communicates with the capillary 5 and is tapered to widen as it extends toward the outside. The bottom wall 72' of the attachment 7 is provided with a through-hole 79' at a location corresponding to the air vent 39'. The mount portion 64' of the blood glucose level measuring apparatus 6' is provided with a through-hole 64a' connected to the air bent 39' and the through-hole 79'. The through-hole 64a' communicates with the interior of the mount portion 64' via a through-hole 64b'. In the air vent 39' and the through-hole 64a', 79' is fitted an open/close pin 69'. The open/close pin 69' is movable reciprocally by a driving mechanism not shown based on instructions from the controller 80 (See FIG. 7). Thus, the air vent 39' of the biosensor X' can be opened or closed by reciprocally moving the open/close pin 69'.

Next, the blood glucose level measuring operation using the blood glucose level measuring apparatus 6' and the attachment 7' will be described. The operation is similar to the first embodiment until an intended amount of blood B is stored in the liquid pooling portion 4 and it is detected by the controller 80 (See FIG. 7).

When the storage of a required amount of blood in the liquid pooling portion 4 is detected, the open/close pin 69' moves upward in the figure based on the instructions from the controller 80 (See FIG. 7) to open the air vent 39'. When the front end of the open/close pin 69' comes to the height of the through-hole 64b', the air bent 39' communicates with the interior of the mount portion 64'. As a result, the blood B retained in the liquid pooling portion 4 quickly flows into the capillary 5 by capillary action, as shown in FIG. 15. The subsequent operation is similar to that of the first embodiment.

In this way, in the blood glucose level measurement using the blood glucose level measuring apparatus 6' and the attachment 7', the blood B is quickly introduced into the capillary 5 after an intended amount of the blood B is stored in the liquid pooling portion 4. Therefore, the time required for blood introduction in the blood glucose level measurement can be prevented from varying largely depending on e.g. the viscosity of the blood B. As a result, accurate measurement can be performed with high reproducibility.

In the foregoing embodiments, the concentration of a particular component is measured by measuring oxidation current using of electrodes. However, the present invention is not limited thereto, and the concentration may be measured utilizing colorimetry. Specifically, in the concentration measurement utilizing colorimetry, a substance is used which changes its color or absorption spectrum when it is oxidized or reduced a result of reduction or oxidation of a substance to be measured.

Although the present invention is described using a biosensor, an attachment and a concentration measuring apparatus for measuring a blood glucose level as an example, the present invention is not limited thereto. For example, the structure of the foregoing embodiments may be utilized for measuring a concentration of cholesterol or lactic acid. Further, the biosensor may be structured as a non-biological sensor which does not contain e.g. enzyme at the reagent portion.

The invention claimed is:

1. A test instrument comprising:
   a capillary for moving a sample liquid;
   a liquid pooling portion communicating with the capillary for retaining the sample liquid to be introduced into the capillary;
   a liquid introduction selector for selecting whether or not the sample liquid retained in the liquid pooling portion is introduced into the capillary;
   a detector for detecting whether or not an intended amount of sample liquid is supplied to the liquid pooling portion; and
   a reagent portion provided in the capillary for dissolution upon supply of the sample liquid to the capillary, and a first measurement electrode and a second measurement electrode for applying a voltage to a reaction system formed by the reagent portion and the sample liquid;
   wherein the detector includes a first detection electrode and a second detection electrode which are exposed to an inside of the liquid pooling portion at least partially, and whether or not an intended amount of sample liquid is supplied to the liquid pooling portion is determined by detecting whether or not electrical conduction through the sample liquid is provided between the first detection electrode and the second detection electrode,
   wherein the first detection electrode is electrically connected to the first measurement electrode, the second detection electrode being electrically connected to the second measurement electrode.

2. The test instrument according to claim 1, further comprising:
   a substrate; and
   a cover for defining the capillary together with the substrate;
   wherein the liquid pooling portion includes an introduction port communicating with the capillary for introducing the sample liquid;
   wherein the introduction port is formed in the substrate; and
   wherein the liquid pooling portion continuously penetrates the substrate and the cover thicknesswise,
   wherein the liquid introduction selector includes a discharge port for discharging air from an inside of the capillary, the discharge port being provided at the substrate and opened away from the cover.

3. The test instrument according to claim 2, wherein the introduction port opens wider than an entrance of the capillary.

4. The test instrument according to claim 2, further comprising a close contact layer which is provided adjacent the introduction port and which is more adherent to skin than the substrate or the cover.

5. The test instrument according to claim 2, wherein the liquid pooling portion has an internal capacity which is generally equal to or larger than an internal capacity of the capillary.

6. An attachment for mounting to a concentration measuring apparatus for measuring concentration of a particular component in a sample liquid, the attachment being provided with a test instrument including a capillary for moving the sample liquid;
   wherein the test instrument comprises a liquid pooling portion communicating with the capillary for retaining the sample liquid to be introduced into the capillary, a liquid introduction selector for selecting whether or not the sample liquid retained in the liquid pooling portion is introduced into the capillary, a detector for detecting whether or not an intended amount of sample liquid is supplied to the liquid pooling portion, a reagent portion provided in the capillary for dissolution upon supply of the sample liquid to the capillary, and first and second measurement electrodes for applying a voltage to a reaction system formed by the reagent portion and the sample liquid;
   wherein the detector includes a first detection electrode and a second detection electrode which are exposed to an inside of the liquid pooling portion at least partially, and whether or not an intended amount of sample liquid is supplied to the liquid pooling portion is determined by detecting whether or not electrical conduction through the sample liquid is provided between the first detection electrode and the second detection electrode,
   wherein the first detection electrode is electrically connected to the first measurement electrode, the second detection electrode being electrically connected to the second measurement electrode.

7. A concentration measuring apparatus for measuring concentration of a particular component in a sample liquid by utilizing an attachment mounted to the concentration measuring apparatus and provided with a test instrument;
   the test instrument comprising a substrate, and a cover for defining a capillary together with the substrate;
   wherein the test instrument comprises the capillary for moving a sample liquid, a liquid pooling portion communicating with the capillary for retaining the sample liquid to be introduced into the capillary, and a liquid introduction selector for selecting whether or not the sample liquid retained in the liquid pooling portion is introduced into the capillary;
   wherein the concentration measuring apparatus further includes a selector for selecting whether or not the sample liquid is introduced into the capillary;
   wherein the liquid introduction selector includes a discharge port for discharging air from an inside of the capillary, the discharge port being provided at the substrate and opened away from the cover; and
   wherein the selector includes an air pump for sucking a skin of a patient in order to close the discharge port with the skin.

* * * * *

UNITED STATES PATENT AND TRADEMARK OFFICE
CERTIFICATE OF CORRECTION

PATENT NO. : 7,640,047 B2 Page 1 of 1
APPLICATION NO. : 10/489397
DATED : December 29, 2009
INVENTOR(S) : Sakata et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1151 days.

Signed and Sealed this

Ninth Day of November, 2010

David J. Kappos
*Director of the United States Patent and Trademark Office*